United States Patent [19]
Donike

[11] 3,954,651
[45] May 4, 1976

[54] SILYATION AGENT FOR GAS CHROMATOGRAPHY

[75] Inventor: Manfred Donike, Duren, Germany

[73] Assignee: Macherey, Nagel & Company, Duren, Germany

[22] Filed: Dec. 20, 1973

[21] Appl. No.: 425,712

[52] U.S. Cl.............................. 252/182; 260/448.2 N; 55/67
[51] Int. Cl.².................. B01D 53/30; B01D 15/08; G01N 31/08; C07F 7/30
[58] Field of Search.............. 252/182; 260/448.2 N; 55/67

[56] References Cited
OTHER PUBLICATIONS
Donike, Journal of Chromatography, Vol. 42, (1969), pp. 103–104.

Primary Examiner—Benjamin R. Padgett
Assistant Examiner—Irwin Gluck

[57] ABSTRACT

A silylation agent for use in gas chromatography is characterized in that it contains fluorine bound to carbon, with the fluorine present in an atomic ratio of fluorine to silicon greater than 4:1. Especially suitable are silyl compounds of the general formula:

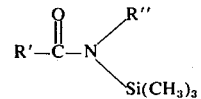

in which R' is fluoro-alkyl, perfluoro-alkyl, fluoro-cyclo-alkyl, perfluoro-cyclo-alkyl, fluoro-aryl, or perfluoro-aryl, and R" is hydrogen or alkyl or cyclo-alkyl or their partially or wholly fluorinated derivatives, and the atomic ratio of fluorine to silicon is greater than 4:1. The alkyl groups may contain 1 to 5 carbon atoms.

11 Claims, 1 Drawing Figure

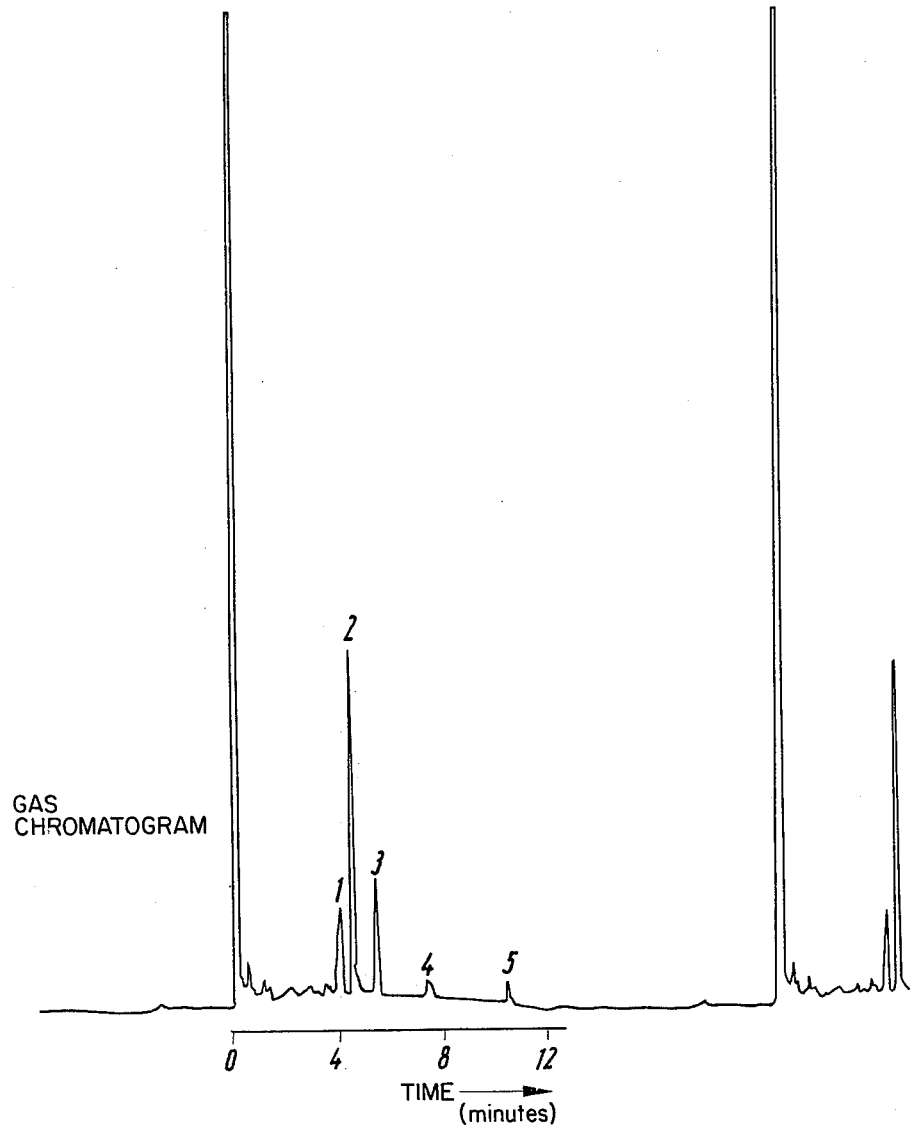

SILYATION AGENT FOR GAS CHROMATOGRAPHY

The present invention concerns a silylation agent suitable for use in gas chromatographic investigations, especially when carried out with the aid of a flame ionization detector. The silyation agent of the invention consists of at least one organic silicon-fluorine compound, as well as, optionally, one or more catalysts and/or dissolving or diluting media.

As is, of course, well known, chromatography is a procedure by which different materials may be spatially separated on an adsorbant. In gas chromatography the material to be separated is in the gaseous phase. An inert gas may be used as a carrier, and a liquid to be analyzed is evaporated into it. The gaseous sample is then flowed into a column containing a substance, such as a high boiling point liquid, in which the materials in the sample have different partition coefficients so that components of the sample are retained in a column for different periods of time, i.e., travel through it at different speeds. A displacement gas may be used to displace components from the column. The differences in retention time and travel through the column may be measured by various apparatus such as thermal conductivity cells, flame ionization detectors, etc. Various techniques in chromatography are of course well known in the art, and need not be further described in detail herein; the silyation agent of the invention is utilizeable in any chromatographic technique wherein silyation is useful.

So-called silylation, that is, the substitution of a silyl group, usually the trimethyl sily group, $-Si(CH_3)_3$, for hydrogen in a compound is a well-known expedient in preparing samples for gas chromatography. Silylation reduces the polarity of the original compound and decreases the possibility of hydrogen bonding. Thus, if the original compound has significant intermolecular hydrogen bonding, the silylated derivative will generally have a higher volatility. Moreover, the stability of the compound is increased by silylation, since the number of points which can be attached by active hydrogen is reduced.

Quite a number of silylation agents have been described; see, for example, *Silylation of Organic Compounds*, by Alan E. Pierce, (1968), Pierce Chemical Co., Rockford, Ill.

Thus, N-methyl-N-trimethyl-silyl trifluoroacetamide (MSTFA) is known as a strong silylation agent, which silylates carboxyl functions quantitatively and, in mixture with trimethyl chlorosilane (TMCS) also transforms alkaline salts of carbonic acids into trimethyl silyl ester. See, Donike, *Journal of Chromatography*, Vol. 42, (1969), pgs. (103–104).

Another known silylation agent for gas chromatographic investigations is bis-trimethyl silyl-trifluoroacetamide (BSTFA); see Stalling et al., *Biochemical and Biophysical Research Communication*, Vol. 3 (1968), pg. 616.

Various characteristics are required for silylation agents, to make them suitable for use in chromatography. They must be available in great purity, and must permit simple production, as rapidly as possible, of the desired silylated derivative. After the conclusion of the gas chromatography, the silyl compound should be capable of being conveniently hydrolyzed to recover the original substance. Finally, the silylation agent should also be readily available in commercial channels.

All these characteristics are provided, to a greater or lesser degree, by the silylation agents in use today.

In gas chromatography with the use of flame ionization dectors however, the known silylation agents have been found disadvantageous in that they lead to a contamination of the equipment, because silyl groups in the silyated compounds are changed by the combusion undergone in the flame ionization detectors, to $SiO_2$. The $SiO_2$ is precipitated from the gas phase and deposits on the exposed parts of the flame ionization detector. This requires frequent cleaning of the apparatus, and even the replacement of expensive detector parts.

The present invention addresses itself to the problem of discovering silylation agents for gas chromatographic investigations, especially for detection with the aid of a flame ionization detector, which, on decomposition, do not lead to the formation of $SiO_2$, or other contaminating or corroding secondary products, but which otherwise have the same advantageous properties as the presently known silylation agents.

This problem is solved, according to the invention, by a novel silylation agent characterized by containing fluorine bound to carbon in an atomic ratio of fluorine to silicon greater than 4:1.

Especially suitable are silyl compounds of the following general formula:

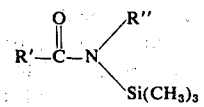

in which R' is fluoro-alkyl, perfluoro-alkyl, fluoro-cyclo-alkyl perfluoro-cyclo-alkyl, fluoro-aryl, or perfluoro-aryl, and R'' is hydrogen or alkyl or cyclo-alkyl or their partially or wholly fluorinated derivatives, and the atomic ratio of fluorine to silicon is greater than 4:1. The alkyl groups may contain 1 to 5 carbon atoms.

Preferably, N-methyl-N-trimethyl silyl-heptafluorobutyric acid amide, of the formula:

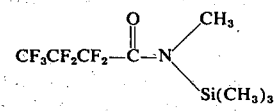

is used, called MSHFBA hereinafter.

This compound can be produced for example, as follows:

Reaction scheme: formulas

Step I:

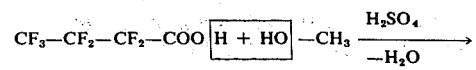

$CF_3-CF_2-CF_2-COO-CH_3$

Step II:

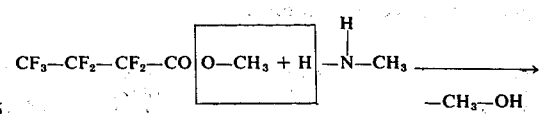

$CF_3-CF_2-CF_2-CO-NH-CH_3$

Step III:

-continued

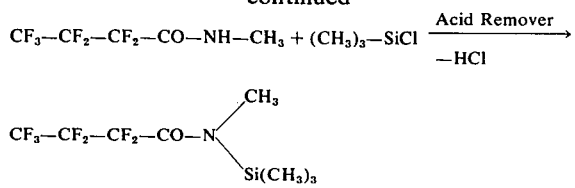

Reaction scheme: description

Step I: Heptafluorobutyric acid methyl ester

Into a mixture of 600 ml acid (about 1 kilogram, equal to about 4.5 mol) and 225 ml methanol (about 179 grams, equal to about 4.5 mol), 150 ml concentrated sulfuric acid is trickled, under agitation, at room temperature. An emulsion is formed, from which then the heptafluorobutyric acid methyl ester in the oil bath can be distilled off with the use of a short column, about 40 cm long, filled with glass Raschig rings. Boiling point, 80°C.
Yield: 1033 grams (about 98%)

Step II: N-methyl-N-heptufluorobutyric acid amide

Into a mixture of 1033 grams heptafluorobutyric acid methyl ester and 500 ml benzol, methyl amine was introduced for about 4 hours, with agitation, at 0°C, until the solution reacted alkaline, (as shown by taking a small sample with a pipette and dripping on a moistened pH paper). Then the benzol was distilled off and the crystallized N-methyl-N-heptafluorobutyric acid amide left behind, was dissolved in 1 liter absolute ethyl acetate. To this solution was added 15 ml trimethyl chlorosilane. After standing a good while (several hours or overnight) the precipitate was filtered out.

Step III: N-methyl-N-trimethyl silyl heptafluorobutyric acid amide

Half of the solution, obtained in Step II, of N-methyl-N-heptafluorobutyric acid amide (about 2.2 mol) in ethyl acetate was treated immediately, in a 4-liter three-necked flask, equipped with an agitator, a reflux cooler and a dripping funnel, with 350 ml triethyl amine (0.2 mol excess).

340 ml trimethyl chlorosilane (0.2 mol excess) were trickled in, at room temperature. The reaction mixture was kept in the refrigerator overnight. The precipitate was filtered out cold and washed with about 500–800 ml benzol or absolute ethyl acetate. The filtrate was subjected to a first distillation, in which a fraction in the interval of 140°–150°C was obtained. The yield was 952 grams to one kilogram heptafluorobutyric acid put in, corresponding to 68% of theory. Rectification was done with a Vigreaux vacuum jacket column, one meter in length.

Th purified product had the following properties:
* Boiling point = 148°–149°C; ** d 20°/4° = 1.255; Molecular Weight =229.1
* At atmospheric pressure, 760 mm Hg.
** Specific gravity at 20°C (Water at 4°C =1.000)
Mass spectrum (mass and intensity in %)

| | | |
|---|---|---|
| M+ | = 299 | (4 %) |
| M+-15 | = 284 | (8 %) |
| M+-169 | = 130 | (21 %) |
| M+-214 (?) | = 85 | (15 %) |
| (CH₃)₂Si+—F | = 77 | (48 %) |
| +Si(CH₃)₃ | = 73 | (100 %) |

Other compounds of the general formula above given can be prepared in a manner similar to the above given reaction scheme. Those compounds are preferred for which the raw materials of the first step are commercially available on the market. Particularly preferred as raw or starting materials are pentafluoropropionic acid and, pentafluorobenzoic acid, which give the following compounds, having similar chromatographic properties, in equally good yield.

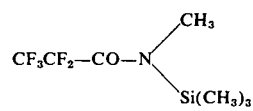

and

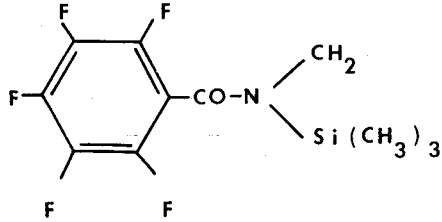

EXAMPLE

The use of one embodiment of a silylation agent in accordance with the invention, in a chromatographic analysis is explained in detail below, and the chromatogram obtained thereby is shown in the accompanying drawing.

A mixture of
1. 30 ppm p-hydroxy amphetamine (1-1-hydroxyphenyl-2-aminopropane)
2. 30 ppm caffeine as internal standard
3. 30 ppm etamivane (diethyl vanilla amide)
4. 5 % tetracosane (C₂₄-n-alkane) and
5. 30 ppm strychnine was subjected to silylation with N-methyl-N-trimethyl silylheptafluorobutyric amide, (MSHFBA), which contained a small amount of trimethyl chlorosilane as catalyst and was diluted with butyl acetate as solvent.

The composition of the silylation mixture was 40% MSHFBA, 1 % trimethyl chlorosilane and 59 % butyl acetate (% by volume).

Detection took place with an alkali flame ionization detector (N-FID) on a Hewlett-Packard gas chromatograph 7600 with automatic injection device. The temperature program was as follows:

150°C, 2 minutes isotherm, 15° C per minute up to 260°C, 4 minutes isotherm.

Analysis cycle: 16 minutes
Number of analyses: 60

The constancy of the N-FID with MSHFBA appears from the following table:

| Compound | Amount determined | Standard deviation S of 56th to 60th analysis rel n= 5 |
|---|---|---|
| p-hydroxyamphetamine | 35 ppm | 1.6 % |
| Caffeine | 30 ppm | 0 % |
| Etamivane | 35 ppm | 2.0 % |
| Tetracosane | 6.0% | 6.2 % |
| Strychnine | 34.5 ppm | 16.0 % |

These values show that the sensitivity of the N-FID has not decreased, since in the low range of concentration, the values put in are found again with an excellent reproducibility; (the lower reproducibility in the case of strychnine is probably due to an erroneous integration.) The standardization changed but little in this duration test of about 18 hours (including the preceding standardization).

The gas chromatogram obtained is shown in the drawing. The numerals 1, 2, 3, 4 and 5 on the drawing show peaks obtained in the chromatogram due to the correspondingly numbered components of the mixture in the example.

Amino acids, phenols, phenolalkyl amine and carbonic acids can be reacted with MSHFBA similarly and with the same result.

MSHFBA may also be used for silylation without addition of catalysts or other silylation agents and/or solvents.

While the invention has been described in detail in connection with specific embodiments thereof, it will be apparent to those skilled in the art upon a reading and understanding of the foregoing disclosure that variations may be made to the specific embodiments shown which variations are nonetheless within the spirit and scope of the appended claims, which are intended to embrace the same.

What is claimed is:

1. A silylation agent suitable for use in gas chromatographic investigations, comprises at least one organic silicon-fluorine compound of the general formula

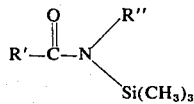

in which R' is selected from the class consisting of fluoro-alkyl, perfluoro-alkyl, fluoro-cyclo-alkyl, perfluoro-cyclo-alkyl, fluoro-aryl, and perfluoroaryl, and R'' is selected from the class consisting of hydrogen, alkyl, cyclo-alkyl and the partially or wholly fluorinated derivatives of alkyl and cyclo-alkyl, and the atomic ratio of fluorine to silicon is greater than 4:1.

2. The silylation agent of claim 1, further including a silylation catalyst and a solvent.

3. The silylation agent of claim 1, wherein the alkyl groups contain from 1 to 5 carbon atoms.

4. The silylation agent of claim 1, wherein the silicon-fluroine compound is N-Methyl-N-trimethyl silyl-heptafluorobutyric acid amide which has the formula

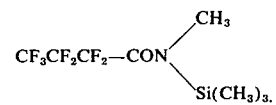

5. The silylation agent of claim 4, further containing trimethyl chlorosilane catalyst and butyl acetate solvent.

6. A method of carrying out gas chromatographic investigation of gaseous samples includes silylating the gaseous samples with a silylation agent which comprises at least one organic silicon-fluorine compound of the general formula

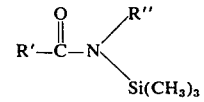

in which R' is selected from the class consisting of fluoro-alkyl, perfluoro-alkyl, fluoro-cyclo-alkyl, perfluoro-cyclo-alkyl, fluoro-aryl, and perfluoro-aryl, and R' is selected from the class consisting of hydrogen, alkyl, cyclo-alkyl and the partially or wholly fluorinated derivatives of alkyl and cyclo-alkyl, and the atomic ratio of fluorine to silicon is greater than 4:1.

7. The method of claim 6 wherein the silylation agent further includes a silyation catalyst and a solvent.

8. The method of claim 6 wherein the alkyl groups contain from 1 to 5 carbon atoms.

9. The method of claim 6 wherein the silicon-fluorine compound is

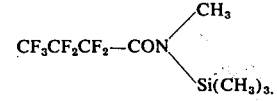

10. The method of claim 9 wherein the catalyst employed is trimethyl chlorosilane and the solvent is butyl acetate.

11. The method of claim 6 further including flame ionization detection of the silylated gaseous sample.

* * * * *